United States Patent [19]

McKinley et al.

[11] Patent Number: 5,220,453
[45] Date of Patent: Jun. 15, 1993

[54] TELESCOPIC SPECTACLES WITH COAXIAL ILLUMINATION

[75] Inventors: Harry R. McKinley, Southampton; Arthur C. McKinley, Haverhill, both of Mass.

[73] Assignee: Luxtec Corporation, Sturbridge, Mass.

[21] Appl. No.: 658,068

[22] Filed: Feb. 20, 1991

[51] Int. Cl.⁵ .................... G02B 27/02; G02B 25/00
[52] U.S. Cl. ........................... 359/481; 359/613; 359/614; 362/268
[58] Field of Search ............ 359/480, 481, 613, 614; 362/268

[56] References Cited

U.S. PATENT DOCUMENTS

| | | | |
|---|---|---|---|
| 3,060,308 | 10/1962 | Fortuna | 240/6.4 |
| 3,586,414 | 6/1971 | Schultz | 359/481 X |
| 3,592,525 | 7/1971 | Schultz | 350/146 |
| 4,086,004 | 4/1978 | Scivo et al. | 351/158 |
| 4,145,122 | 3/1979 | Rinard et al. | 351/7 |
| 4,195,918 | 4/1980 | Freche et al. | 351/158 |
| 4,196,966 | 4/1980 | Malis | 350/145 |
| 4,274,128 | 6/1981 | Malis | 362/105 |
| 4,360,253 | 11/1982 | Wyatt | 351/158 |
| 4,364,645 | 12/1982 | Feinbloom | 351/204 |
| 4,621,283 | 11/1986 | Feinbloom | 358/93 |
| 4,626,257 | 10/1986 | Kloots et al. | 358/93 |
| 4,705,366 | 11/1987 | Kimura et al. | 350/529 |
| 4,714,321 | 12/1987 | Sillitto | 350/174 |
| 4,807,987 | 2/1989 | Bastable et al. | 351/205 |

Primary Examiner—Scott J. Sugarman
Attorney, Agent, or Firm—Weingarten, Schurgin, Gagnebin & Hayes

[57] ABSTRACT

A coaxial illuminator adapted for surgical coaxial illumination and viewing including an opaque housing defining a longitudinal axis and having a tilted, anti-reflection coated window located at one end of the housing. A beamsplitter is located within the housing and is positioned so as to reflect light, from a light source, along the longitudinal axis of the housing through the window to illuminate the object and to permit image light from the object being viewed to pass along the longitudinal housing through the beamsplitter. An absorber is positioned to absorb light which passes from the light source through the beamsplitter unreflected.

7 Claims, 3 Drawing Sheets

TELESCOPIC SPECTACLES WITH COAXIAL ILLUMINATION

This invention relates to telescopic spectacles.

BACKGROUND OF THE INVENTION

Telescopic spectacles are used by surgeons and others who must work with minute objects. Typically the telescopes are arranged either in pairs, with one telescope positioned for viewing by each eye of the wearer, or alternatively, with a single telescope positioned in the center of the spectacles. The image path from the single telescope is divided into two images, with one image being viewed by each eye. Telescopic spectacles may be constructed either with or without an integral object illuminator.

When the illumination, either supplied by a light source which is integral with the telescopic spectacles or otherwise provided externally, does not illuminate the object to be viewed along the viewing image path, portions of the object in the light path cast shadows. The casting of shadows increases the difficulty in viewing other portions of small objects, for example within an operating field. Shadows are least when the illumination beam and the viewing image path are coaxial and they increase in size as the angle of divergence between the illumination beam and the viewing image path increases.

Examples of providing the illumination and the image viewing path coaxial by using beamsplitters are shown in the commonly assigned applications Ser. No. 07/419,896, filed Oct. 11, 1989 and Ser. No. 07/419,761, filed Oct. 11, 1989. The present invention discloses a coaxial illuminator which permits illumination of an object along the image viewing path while reducing the amount of light reflected into the eyes of the user.

SUMMARY OF THE INVENTION

In one aspect, the invention is a pair of telescopic spectacles with a coaxial illuminator. The telescopic spectacles include, a telescope positioned so as to produce, for viewing by a wearer, the image of an object to be viewed and a coaxial illuminator, positioned so as to permit the coaxial illumination of the object. The coaxial illuminator includes an opaque housing defining a longitudinal axis, and an anti-reflection coated window located at one end of the housing. The window is tilted at an angle such that a normal to the surface of the window is not coincident with the longitudinal axis of the housing. A beamsplitter is located within the housing and positioned so as to reflect light from an illumination lens, along the longitudinal axis of the housing through the window to illuminate the object, and to permit image light from the object being viewed to pass along the longitudinal axis of the housing through the beamsplitter to the telescope. The illumination lens is located so as to project light from an optical fiber onto the beamsplitter. An absorber is positioned so as to absorb light which passes from the illuminating lens through the beamsplitter unreflected.

In another aspect, the invention is a coaxial illuminator positioned so as to permit the coaxial illumination of an object to be viewed. The illuminator includes an opaque housing defining a longitudinal axis, a window located at one end of the housing, and a beamsplitter. The beamsplitter is located within the housing and positioned so as to reflect light from a light source along the longitudinal axis of the housing through the window to illuminate the object, and to permit image light from the object being viewed to pass along the longitudinal axis of the housing through the beamsplitter. An absorber is positioned to absorb light which passes from the light source through the beamsplitter unreflected.

BRIEF DESCRIPTION OF THE DRAWINGS

Other features and benefits of the invention can be more clearly understood with reference to the specification and the accompanying drawings in which.

DESCRIPTION OF THE PREFERRED EMBODIMENT

Figure 1:
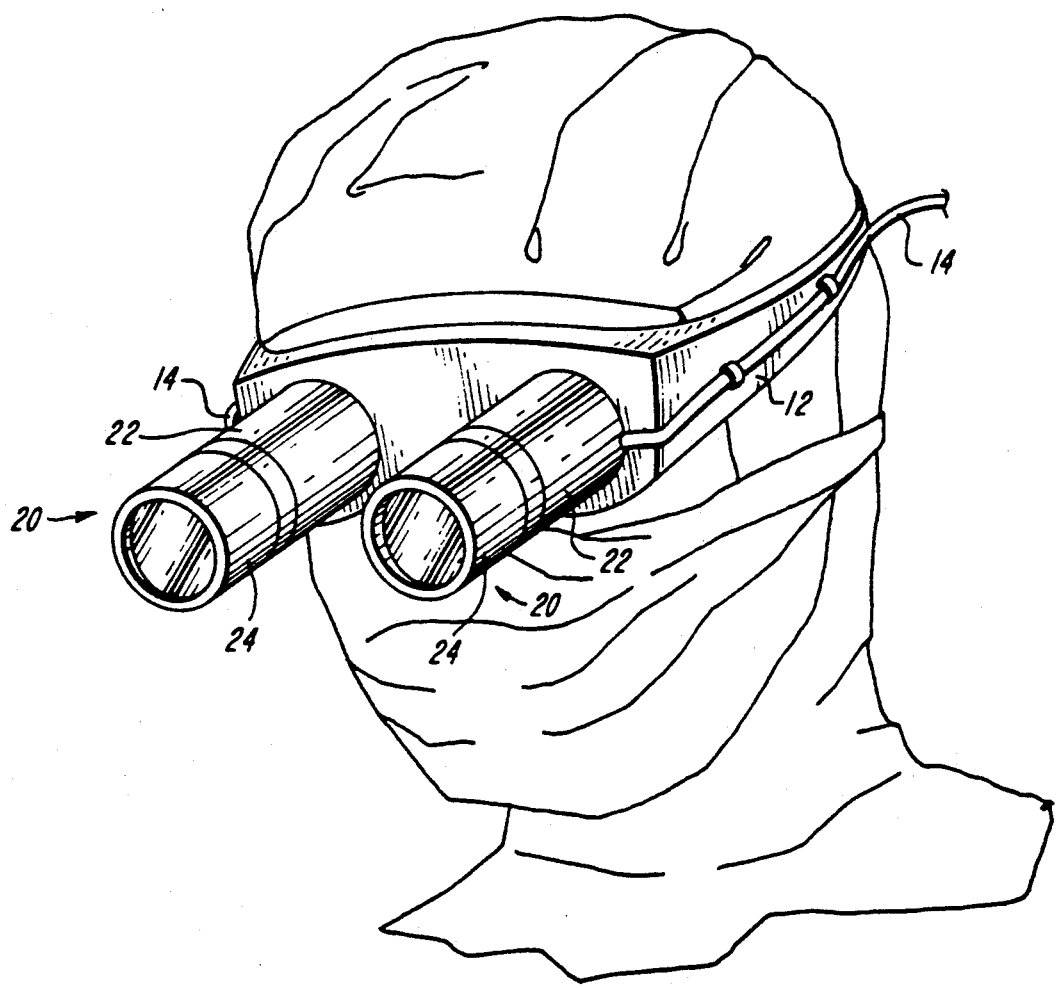
FIG. 1 is a perspective drawing of an embodiment of the invention used with each of a pair of telescopes.

Referring to FIG. 1, one embodiment of the telescopic spectacles with coaxial illumination 10 includes a pair of illuminator/telescope portions 20. The illuminator/telescope portion 20 includes an illumination portion 24 and a telescope 22. The embodiment of the telescopic spectacles 10 shown in FIG. 1, is held in place by a retaining strap 12. The strap 12 holds the pair of illuminator telescope portions 20 positioned adjacent the eyes of the wearer.

Figure 2:
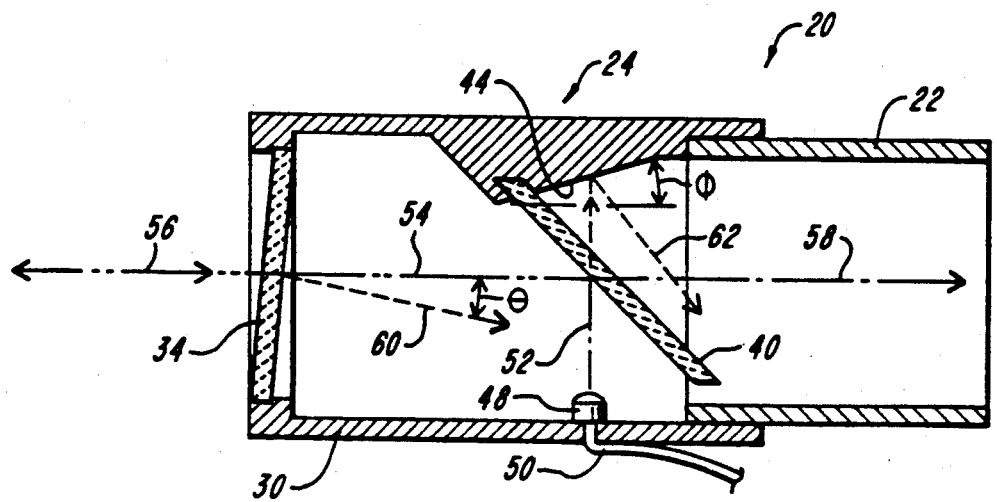
FIG. 2 is a schematic view of the illumination portion of the invention as shown in the embodiment in FIG. 1.

Considering each portion of the illuminator/telescope portion 20 in more detail, and referring to FIG. 2, the illumination portion 24 of the illuminator/telescope 20 includes, in one embodiment, an opaque cylindrical housing 30 sealed at one end by a forward exit window 34. The forward exit window 34 has a non-reflective coating and is tilted with respect to the axis of the housing 30. The tilt is such that a normal to the surface of the forward exit window 34 is not coincident with the axis of the housing 30. The other end of the housing 30 abuts and is closed by the telescope 22. The housing 30 is aligned with the telescope 22 such that the axis of the housing 30 and the axis of the telescope 22 are coaxial.

Located within the housing 30, intermediate between the forward exit window 34 and the telescope 22, is a beamsplitter 40. The beamsplitter 40, most simply, is a thin film coated flat plate which partially transmits light incident upon it. The beamsplitter 40, shown is oriented at about 45° with respect to the axis of the housing 30. That is, a normal to the surface of the beamsplitter 40 is oriented off-axis from the axis of the housing 30 by 45°.

Positioned near the wall of the housing 30 is a lens assembly 48 which projects light from an optical fiber 50 toward the beamsplitter 40. The source of light for the optical fiber 50 may be located within the spectacles. Alternatively, the light source may be external to the spectacles and the light transmitted into the illumination portion 24 of the spectacles through an optical fiber 14 such as shown in FIG. 1.

Light from the lens assembly 48 is reflected in a forward direction 54 by the beamsplitter 40 and is projected through the exit window 34 to illuminate the object being viewed. Any light 60 reflected by the surface of the exit window 34 is reflected off-axis (angle $\theta$)

due to the tilt in the exit window 34 with respect to the axis of the housing 30. Therefore, light reflected by the exit window 34 does not reflect back along the image path 58 into the telescope 22.

Light from the lens assembly 48, which is not reflected but which passes through the beamsplitter 40, impinges upon an absorber 44. The absorber 44 is also tilted (angle $\phi$) so that any light 62 reflected by the surface of the absorber 44 is also not reflected along the beam path 52 leading from the lens 48 to the absorber 44. This assures that when the light, which is reflected from the surface of the absorber 44, is then reflected by the beamsplitter 40, the light reflected by the beamsplitter 40 is then also reflected off-axis, relative to the axis of the housing 30, and therefore is not reflected along the image beam path 52 into the telescope 22. The absorber may be made of a flat black material to reduce the amount of reflection.

The elements 34, 40 and 44 are tilted, preferably at angles so as to minimize the flare or extraneous light that is perceived by the observer through the telescope. One way to obtain good results includes empirical placement using ray tracing algorithms that minimize the flare rays observed.

Figure 1A:
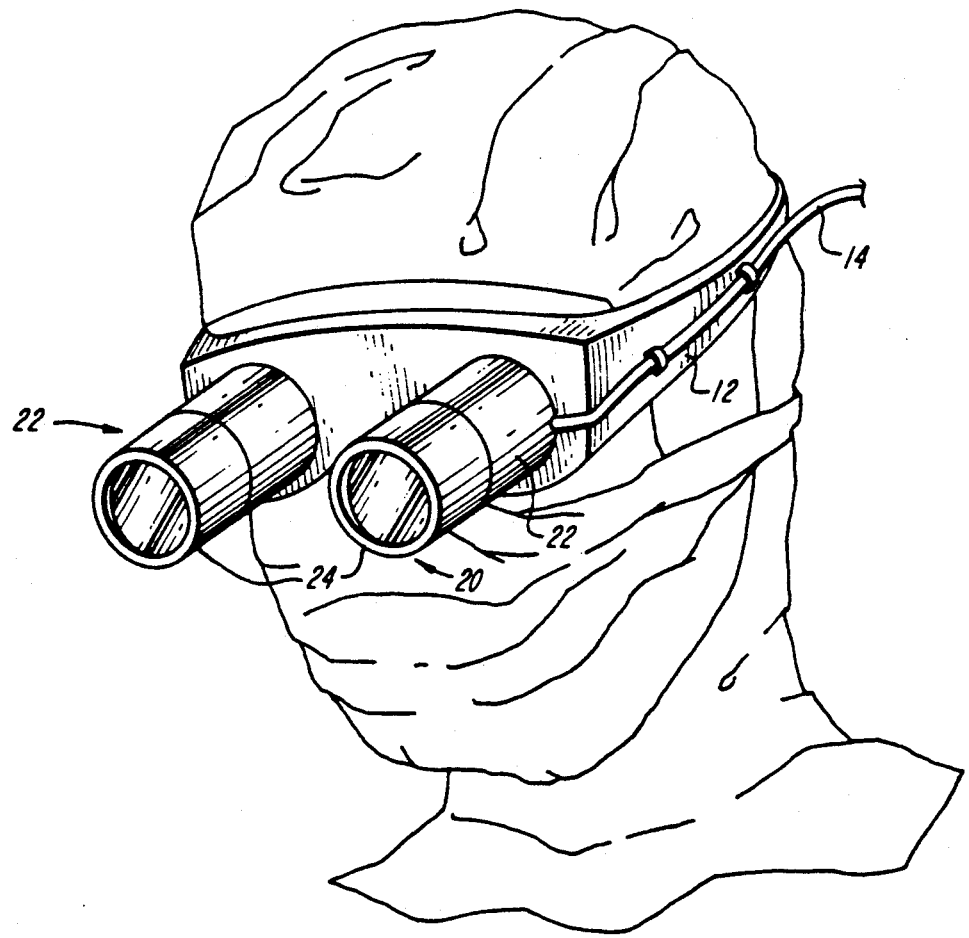
FIG. 1a is a perspective view of an embodiment of the invention used with one of a pair of telescopes.
Figure 3:
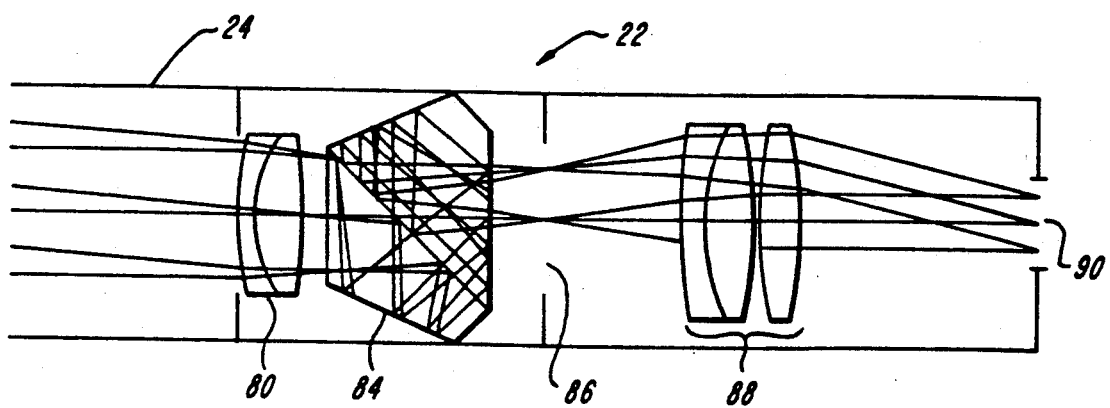
FIG. 3 is a highly schematic view of an embodiment of the optical train of the telescope portion of the embodiment of the invention shown in FIG. 1.
Figure 4:
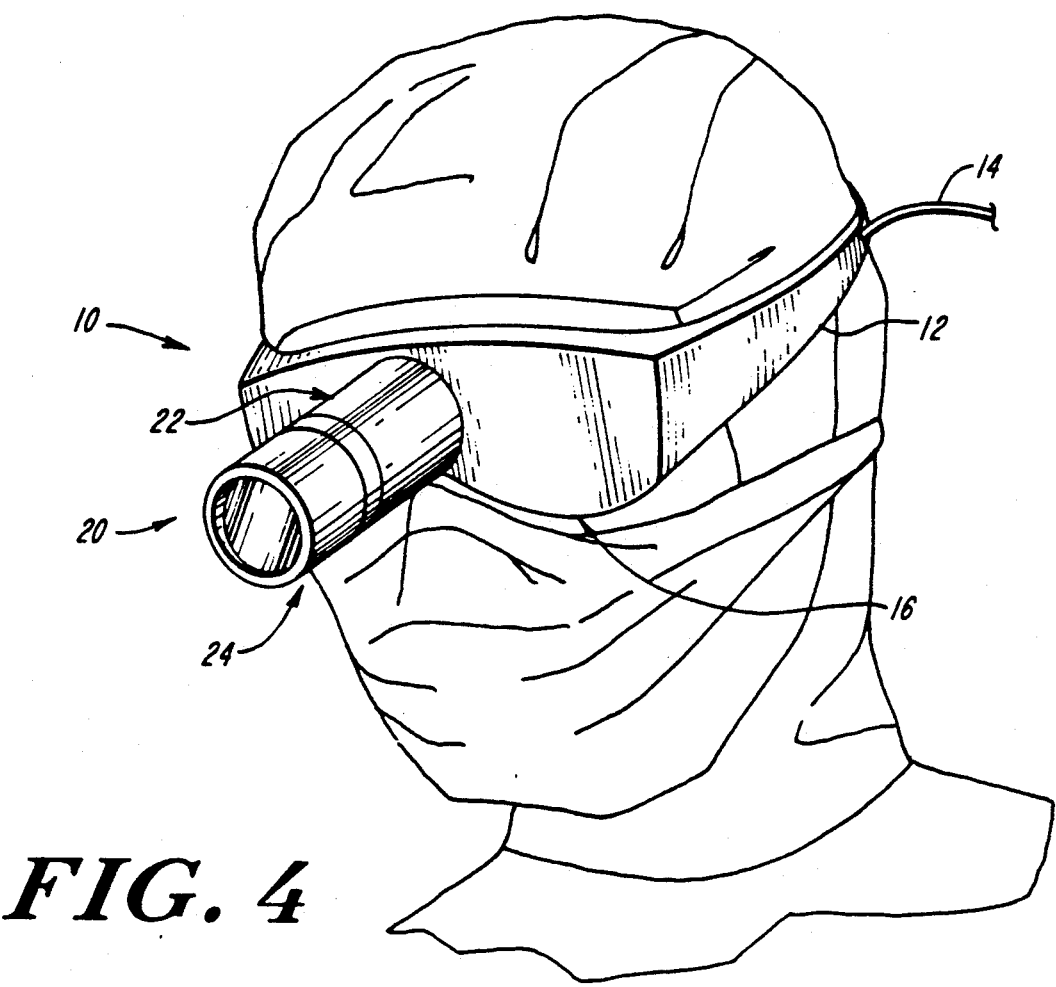
FIG. 4 is a perspective drawing of an embodiment of the invention being used with a central single telescope.

An embodiment of a telescope 22 suitable for use with the previously described illuminator 24 is shown in FIG. 3. This embodiment is a light weight, 2.5X-power telescope 22 which includes an objective lens 80, a pechan roof prism 84 and an eyepiece assembly 88. Image light 57, passing through the beamsplitter 40 from the forward exit window 34, passes into the telescope 22 through the objective lens 80. The image beam path then undergoes multiple foldings within the pechan prism 84 and passes through a field stop 86. The light which exits through the field stop 86 is gathered by the eyepiece 88 and focussed at the exit pupil 90. Although the illuminator discussed above is disclosed in conjunction with this telescope, the illuminator may be used with any telescope. Further, although the coaxial illuminator is depicted in conjunction with each (FIG. 1) telescope of a pair of telescopes, it may also be used in conjunction with only one telescope of a pair of telescopes (FIG. 1a) or with a single telescope centrally mounted to a pair of viewing binoculars (FIG. 4).

These and other examples of the concept of the invention illustrated above are intended by way of example and the actual scope of the invention is to be determined solely from the following claims.

What is claimed is:

1. A pair of telescopic spectacles with coaxial illumination comprising:
    a telescope positioned so as to produce, for viewing along a viewing axis by a wearer, an image of an object to be viewed; and
    a coaxial illuminator positioned so as to permit the coaxial illumination of the object to be viewed by said telescope, said coaxial illuminator comprising:
    an opaque housing defining a viewing axis;
    an anti-reflection coated window located at one end of said housing, said window being tilted at an angle such that a normal to the surface of the window is not coincident with the viewing axis of said housing;
    a beamsplitter located within said housing and positioned so as to reflect light from an illumination lens along the viewing axis of said housing through said window to illuminate the object, and to permit image light from the object being viewed to pass along the viewing axis of said housing through said beamsplitter to said telescope, said illumination lens located so as to project light from an optical fiber onto the beamsplitter; and
    an absorber positioned so as to absorb light which passes from said illuminating lens unreflected through said beamsplitter, said absorber being tilted so that any light reflecting from said absorber is not primarily reflected within said housing into coincidence with the viewing axis toward said telescope.

2. A coaxial illuminator positioned so as to permit the coaxial illumination of an object to be viewed along a viewing axis, said illuminator comprising:
    an opaque housing defining a viewing axis;
    a window located at one end of said housing,
    a beamsplitter located within said housing and positioned so as to reflect light from a light source along the viewing axis of said housing through said window to illuminate said object and to permit image light from the object being viewed to pass along the viewing axis of said housing through said beamsplitter; and
    an absorber positioned to absorb light which passes from said light source through said beamsplitter unreflected.

3. The illuminator of claim 2 wherein said window being tilted at an angle such that a normal to the surface of the window is not coincident with the viewing axis of said housing.

4. The illuminator of claim 2 wherein said light source comprises an optical fiber.

5. The illuminator of claim 4 wherein the light source further comprises an illumination lens for projecting light from the optical fiber onto the beamsplitter.

6. The illuminator of claim 2 wherein said window has an anti-reflection coating.

7. The illuminator of claim 2 wherein said absorber is tilted such that light reflecting from said absorber is not primarily reflected within said housing into coincidence with the viewing axis of said housing.

* * * * *